United States Patent [19]
Steidle

[11] Patent Number: 4,611,585
[45] Date of Patent: Sep. 16, 1986

[54] MOTOR-DRIVEN CUTTER FOR THE CUTTING OPEN OF PLASTER CASTS

[75] Inventor: Gerhard Steidle, Bad Dürrheim, Fed. Rep. of Germany

[73] Assignee: Aesculap-Werke AG vormals Jetter & Scheerer, Tuttlingen, Fed. Rep. of Germany

[21] Appl. No.: 632,035

[22] Filed: Jul. 18, 1984

[30] Foreign Application Priority Data

May 19, 1984 [DE] Fed. Rep. of Germany ....... 3418785

[51] Int. Cl.⁴ ............................................. A61F 5/04
[52] U.S. Cl. ..................................... 128/91 A; 30/124
[58] Field of Search ............. 128/91 A, 317, 83, 91 R; 30/124, 390

[56] References Cited

U.S. PATENT DOCUMENTS

| 2,217,923 | 10/1940 | Silverman . | |
| 3,353,266 | 11/1967 | Goolsby | 128/91 A |
| 4,411,067 | 10/1983 | Kirk | 128/91 A |
| 4,421,111 | 12/1983 | Rothman | 128/91 A |

FOREIGN PATENT DOCUMENTS

| 505274 | 8/1930 | Fed. Rep. of Germany . | |
| 719969 | 4/1942 | Fed. Rep. of Germany . | |
| 888595 | 9/1953 | Fed. Rep. of Germany ... | 128/91 A |
| 3101363 | 12/1981 | Fed. Rep. of Germany . | |
| 731182 | 6/1955 | United Kingdom ............ | 128/91 A |

OTHER PUBLICATIONS

Brochure, Aesculap—Oscillant Pendula II "Electrical Plaster Saws", Aesculap-Werke AG D-7200 Tuttlingen/Fed. Rep. of Germany.

Primary Examiner—Gene Mancene
Assistant Examiner—Wenceslao J. Contreras
Attorney, Agent, or Firm—Kenway & Jenney

[57] ABSTRACT

In a motor-driven cutter for the cutting open of plaster casts with a motor housing, a fixed center blade and two oscillatingly motor-driven blades disposed either side of the fixed blade and both interacting with said fixed blade and moving the cutter forward along the cut, in order to prevent unitentional contacting of the blades, it is proposed that a cover hood be displaceably mounted on the motor housing and be displaced by a flexible force storage means into a position covering the three blades whereby the cover hood exhibits glide-on surfaces which, as the cutter is pushed forward, glide on the plaster, thereby displacing the cover hood against the action of the flexible force storage means into a position exposing the blades.

6 Claims, 3 Drawing Figures

MOTOR-DRIVEN CUTTER FOR THE CUTTING OPEN OF PLASTER CASTS

The invention relates to a motor-driven cutter for the cutting open of plaster casts with a motor housing, a fixed centre blade and two oscillatingly motor-driven blades disposed either side of the fixed blade and both interacting with said fixed blade and moving the cutter forward along the cut.

Such a cutter is known, for example, from German patent specification No. 719 969. Such cutters have proved highly successful for the cutting open of plaster casts since they cut a strip out of the plaster cast, thus making it particularly easy to remove a plaster cast.

The object of the invention is to protect the operator from unintentionally coming into contact with the moving blades which additionally exhibit sharp teeth.

The object of the invention is achieved in a cutter of the initially described kind in that a cover hood is displaceably mounted on the motor housing and is displaced by a flexible force storage means into a position covering the three blades whereby the cover hood exhibits glide-on surfaces which, as the cutter is pushed forward, glide on the plaster and displace the cover hood against the action of the flexible force storage means into a position exposing the blades.

Such a cover hood ensures that the blades are exposed only when the cutter is applied to the plaster cast itself whereby in this case the parts of the blades disposed above the plaster are still encompassed by the cover hood so that there is no possibility from outside of coming into contact unintentionally with the blades.

It is advantageous if the cover hood is mounted on a cover shell which covers a gear drive of the knives and is releasably connected to the remaining motor housing. Such a cover shell is normally provided on plaster cutters of this kind so that there is easy access to the gear drive in order, for example, to be able to perform maintenance operations or to be able to exchange parts. If the cover hood is mounted on this cover shell, cover hood and cover shell can be removed simultaneously so that there is then access to the gear drive and the blades driven by the gear drive.

The cover hood may exhibit two parallel walls which extend parallel to the blades and are connected to a cross-wall on their side facing away from the housing.

The cover hood can be manufactured and mounted with particular ease if it consists of two shells of mirror image construction.

In a preferred embodiment each shell bears a web directed toward the other shell whereby said webs are inserted in guide grooves on the motor housing.

The cover hood can be mounted in extremely simple manner if the two shells are guided against each other whereby the webs are inserted in the guide grooves. Then the two shells are connected to each other, for example by means of a latch-type connection or by means of a screw connection.

Preferably, the guide grooves may be formed by a cross-sectionally T-shaped bar on the motor housing, said bar bearing at each of its ends a face wall acting as a stop. Such a T-shaped bar can easily be moulded onto the motor housing.

In a preferred embodiment the glide-on surfaces are formed by two arc-shaped edges on the underside of the side walls.

In a preferred embodiment the cover hood is in the form of an L-shape whereby a first leg extends parallel to the direction of displacement of the cover hood mounting and provides the mounting on the motor housing while the second leg on the underside of the motor housing extends opposite to the cutting direction of the cutter.

It is advantageous if the first leg becomes increasingly wider toward the other leg. Preferably, the second leg exhibits the glide-on surfaces.

With reference to the drawings, the following description of a preferred embodiment describes the invention in greater detail.

Figure 1:
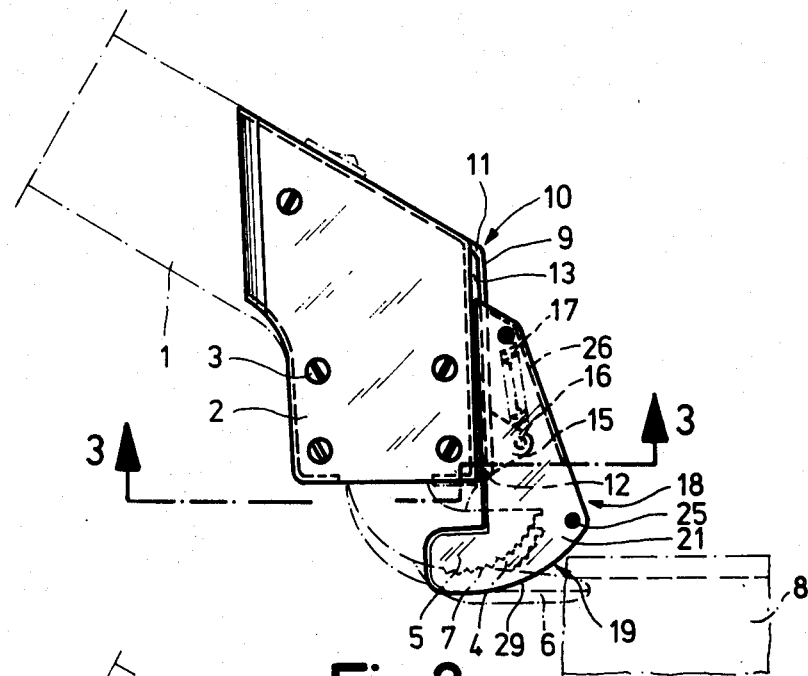
FIG. 1 shows a side view of the front part of a plaster cutter with cover hood lowered.

The drawing shows only the head of the plaster cutter; the actual motor housing 1 is reproduced only schematically by a dash-dotted line. The motor housing 1 is usually considerably larger than the head and is in the form of a handle part in which the motor is housed. The only part of the motor housing shown in the drawing is a cover shell 2 which is attached by means of screws 3 to the remaining motor housing and covers a gear drive (not shown in the drawing) which drives two oscillatingly driven blades 4 and 5 which are mounted on the motor housing either side of a fixed blade 6 in the part covered by the cover shell 2. The fixed blade 6 and the two oscillatingly driven blades 4 and 5 project downward out of the cover shell 2 and are bent toward the front side of the cutter. On their arc-shaped bottom edge the two oscillating blades 4 and 5 bear teeth 7 which, during the oscillating movement, rest on the surface of the plaster 8 and move the cutter forward along the cut as a result of the oscillating movement. The fixed blade 6 dips under the plaster so that the moving blades and the fixed blade interact and cut open the plaster between them.

The cover shell 2 which is screwed onto the side of the remaining motor housing bears at its front end edge 9 a vertically extending bar 10 of T-shaped cross section which is provided at each of its two ends with a cross-wall 11, 12. Thus, on either side of the cover shell 2 there are vertical guide grooves 13, 14 which are terminated at their ends by the cross-walls 11 and 12 respectively.

Moulded onto the T-shaped bar 10 in its lower region is a projection 15 with an opening 16 through which one end of a tension spring 17 is inserted. The cover shell is preferably made in one piece and of plastic.

Displaceably mounted on the cover shell parallel to the guide grooves 13 and 14 is a cover hood 18 which consists of two mirror-image halves 19 and 20 which both exhibit basically L-shaped side walls 21 and 22 respectively. On its inside edge the first leg exhibits inward-projecting guide ribs 23 and 24 which are inserted in the guide grooves 13 and 14 when the two halves are connected together by means of a latch-type connection or by means of screws 25. Inwardly-facing lip regions 26 and 27 on the outer edges of the first leg form a cross-wall 28 which connects the two side walls of the cover hood. These lip regions 26 and 27 are absent in the lower region where the cover hood consists only of the side walls.

Figure 2:
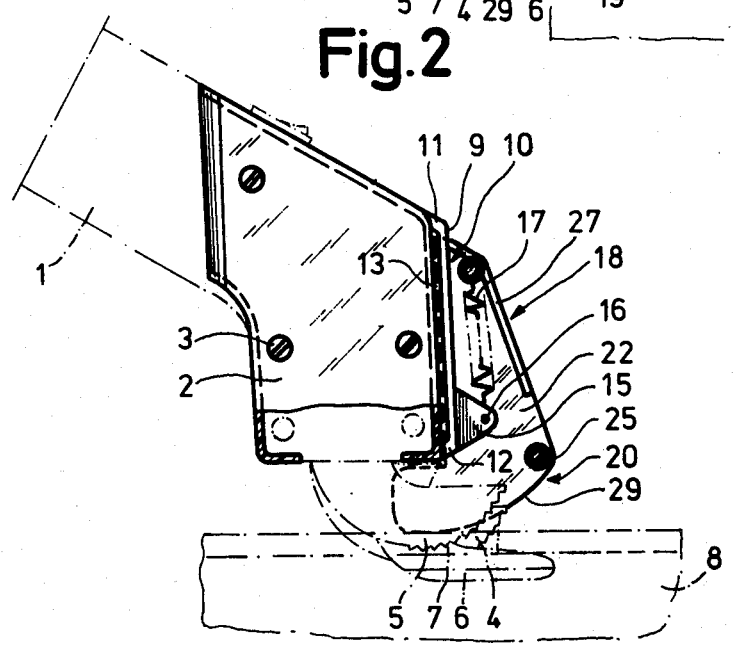
FIG. 2 shows a view similar to FIG. 1 with raised cover hood for cutting the plaster.
Figure 3:
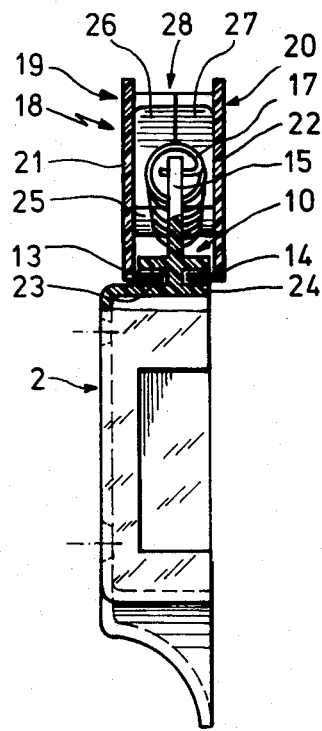
FIG. 3 shows a sectional view on line 3—3 in FIG. 1.

The first legs become increasingly wider toward the second leg, as can be clearly seen from FIGS. 1 and 2.

The second legs extend below the cover shell 2 opposite to the cutting directing and exhibit a bent bottom edge 29 which acts as a glide-on surface.

The other end of the tension spring 17 is attached to the top edge of the cover hood so that the cover hood is displaced by the tension spring 17 into a lower position which is defined by the stop of the guide ribs 23 and 24 on the lower cross-wall 12. In this position the side walls 21 and 22 conceal the blades 4, 5 and 6 particularly in the region of the second legs, and particularly those areas of the blades which are provided with teeth 7 (FIG. 1).

When the cutter is pushed against the plaster which is being cut, the bottom edges 29 glide on the surface of the plaster, thereby displacing the cover hood on the cover shell against the action of the tension spring 17 (FIG. 2). The blades are exposed to such an extent that they are able to execute their cutting action without the user running the risk of coming into direct contact with the blades.

As soon as the cutting operation is completed the tension spring 17 pulls the cover hood back into the lower, concealing position.

The cover hood conceals the blades on both sides and, after loosening the screws 3, can easily be lifted off the motor housing together with the cover shell so that there is access to the blades and the gear drive which is situated under the cover shell. It is also possible in simple manner to remove the cover hood from its mounting or to use a differently shaped cover hood. To do this, it is sufficient to detach the two halves of the cover hood from each other and to remove them laterally from each other so that the guide ribs 23 and 24 are raised out of the corresponding guide grooves 13 and 14 respectively. It is thus also easily possible to use the plaster cutter with or without cover hood, as desired.

What is claimed is:

1. Motor-driven cutter for the cutting open of plaster casts with a motor housing, a fixed centre blade and two oscillatingly motor-driven blades disposed either side of the fixed blade and both interacting with said fixed blade and moving the cutter forward along the cut, comprising:

a cover hood displaceably mounted on the motor housing having glide-on surfaces disposed to contact the plaster, flexible force storage means that acts on said cover hood to displace it into a position covering the three blades whereby the cover hood presents the glide-on surfaces which, as the cutter is pushed forward, glide on the plaster and displace the cover hood against the action of the flexible force storage means into a position exposing the blades, said cover hood consisting of two shells of mirror image construction and having two parallel side walls which extend parallel to the blades and connect to a cross-wall on their sides facing away from the motor housing, and each said shell bearing a web directed toward the other shell whereby said webs are inserted in guide grooves on the motor housing.

2. Cutter as defined in claim 1, wherein the guide grooves (13, 14) are formed by a cross-sectionally T-shaped bar (10) on the motor housing (1), said bar bearing at each of its ends a face wall (11, 12) acting as a stop.

3. Cutter as defined in claim 2, wherein the glide-on surfaces are formed by two arc-shaped edges (29) on the underside of the side walls (21, 22).

4. Cutter as defined in claim 1, wherein the cover hood (18) is in the form of an L-shape whereby a first leg extends parallel to the direction of displacement of the cover hood mounting and provides the mounting on the motor housing (1) while the second leg on the underside of the motor housing (1) extends opposite to the cutting direction of the cutter.

5. Cutter as defined in claim 4, wherein the first leg becomes increasingly wider toward the other leg.

6. Cutter as defined in claim 5, wherein the second leg exhibits the glide-on surfaces (edges 29).

* * * * *